(12) United States Patent
Tinger et al.

(10) Patent No.: US 9,517,980 B2
(45) Date of Patent: Dec. 13, 2016

(54) PROCESS AND APPARATUS FOR THE PRODUCTION OF PARA-XYLENE

(71) Applicant: ExxonMobil Chemical Patents Inc.

(72) Inventors: Robert G. Tinger, Friendswood, TX (US); Dana L. Pilliod, League City, TX (US); Michel Molinier, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/969,327

(22) Filed: Dec. 15, 2015

(65) Prior Publication Data

US 2016/0318827 A1    Nov. 3, 2016

Related U.S. Application Data

(60) Provisional application No. 62/154,774, filed on Apr. 30, 2015.

(51) Int. Cl.

| | |
|---|---|
| *C07C 5/22* | (2006.01) |
| *C07C 4/12* | (2006.01) |
| *C07C 7/12* | (2006.01) |
| *C07C 5/27* | (2006.01) |
| *B01J 19/24* | (2006.01) |
| *B01D 3/14* | (2006.01) |
| *B01D 15/18* | (2006.01) |

(52) U.S. Cl.
CPC ............... *C07C 5/2767* (2013.01); *B01D 3/14* (2013.01); *B01D 15/185* (2013.01); *B01J 19/2445* (2013.01); *C07C 5/2729* (2013.01); *B01J 2219/24* (2013.01)

(58) Field of Classification Search
CPC ................. C07C 5/02; C07C 4/12; C07C 7/12
USPC ............... 585/302, 304, 478, 477, 483, 828
See application file for complete search history.

(56) References Cited

U.S. PATENT DOCUMENTS

2014/0155667 A1    6/2014 Ou et al.

FOREIGN PATENT DOCUMENTS

| WO | WO2012058108 | 5/2012 |
|---|---|---|
| WO | 2016/134055 | 8/2016 |

OTHER PUBLICATIONS

U.S. Appl. No. 14/743,048, filed Jun. 18, 2015, Vander Pol et al.

*Primary Examiner* — Thuan D Dang (57) ABSTRACT

The present invention is an improved process and apparatus for producing para-xylene, particularly with respect to a process that involves the methylation of toluene and/or benzene to selectively produce para-xylene, wherein streams having differing amounts of ethylbenzene are separately treated in the recovery of para-xylene. A first hydrocarbon feed comprising xylenes and ethylbenzene is provided to a first para-xylene adsorption section, and a second hydrocarbon feed comprising xylenes and less EB than the first hydrocarbon feed is provided to a second para-xylene adsorption section. Segregating the feeds with differing ethylbenzene contents increases the overall efficiency of the adsorption of para-xylene by the adsorption units. Efficiency and energy savings may be further improved by subjecting the lower-content ethylbenzene stream to liquid phase isomerization.

15 Claims, 5 Drawing Sheets

PROCESS AND APPARATUS FOR THE PRODUCTION OF PARA-XYLENE

CROSS-REFERENCE OF RELATED APPLICATIONS

This application claims the benefit of Provisional Application No. 62/154,774, filed Apr. 30, 2015.

FIELD OF THE INVENTION

This application relates to an improved process and apparatus for producing para-xylene, particularly the recovery of para-xylene from streams having differing amounts of ethylbenzene.

BACKGROUND OF THE INVENTION

Ethylbenzene (EB), para-xylene (PX), ortho-xylene (OX) and meta-xylene (MX) are often present together in $C_8$ aromatic product streams from chemical plants and oil refineries. Although high purity EB is an important raw material for the production of styrene, for a variety of reasons all high purity EB feedstocks used in styrene production are produced by alkylation of benzene with ethylene, rather than by recovery from a $C_8$ aromatics stream. Of the three xylene isomers, PX has the largest commercial market and is used primarily for manufacturing terephthalic acid and terephthalate esters for use in the production of various polymers such as poly(ethylene terephthalate), poly(propylene terephthalate), and poly(butene terephthalate). While OX and MX are useful as solvents and raw materials for making products such as phthalic anhydride and isophthalic acid, market demand for OX and MX and their downstream derivatives is much smaller than that for PX.

Given the higher demand for PX as compared with its other isomers, there is significant commercial interest in maximizing PX production from any given source of $C_8$ aromatic materials. However, there are a number of major technical challenges to be overcome in achieving this goal of maximizing PX yield. For example, the four $C_8$ aromatic compounds, particularly the three xylene isomers, are usually present in concentrations dictated by the thermodynamics of production of the $C_8$ aromatic stream in a particular plant or refinery. As a result, the PX production is limited, at most, to the amount originally present in the $C_8$ aromatic stream unless additional processing steps are used to increase the amount of PX and/or to improve the PX recovery efficiency. A variety of methods are known to increase the concentration of PX in a $C_8$ aromatics stream. These methods normally involve cycling the stream between a separation step, in which at least part of the PX is recovered to produce a PX-depleted stream, and a xylene isomerization step, in which the PX content of the PX-depleted stream is returned back towards equilibrium concentration.

Figure 1:
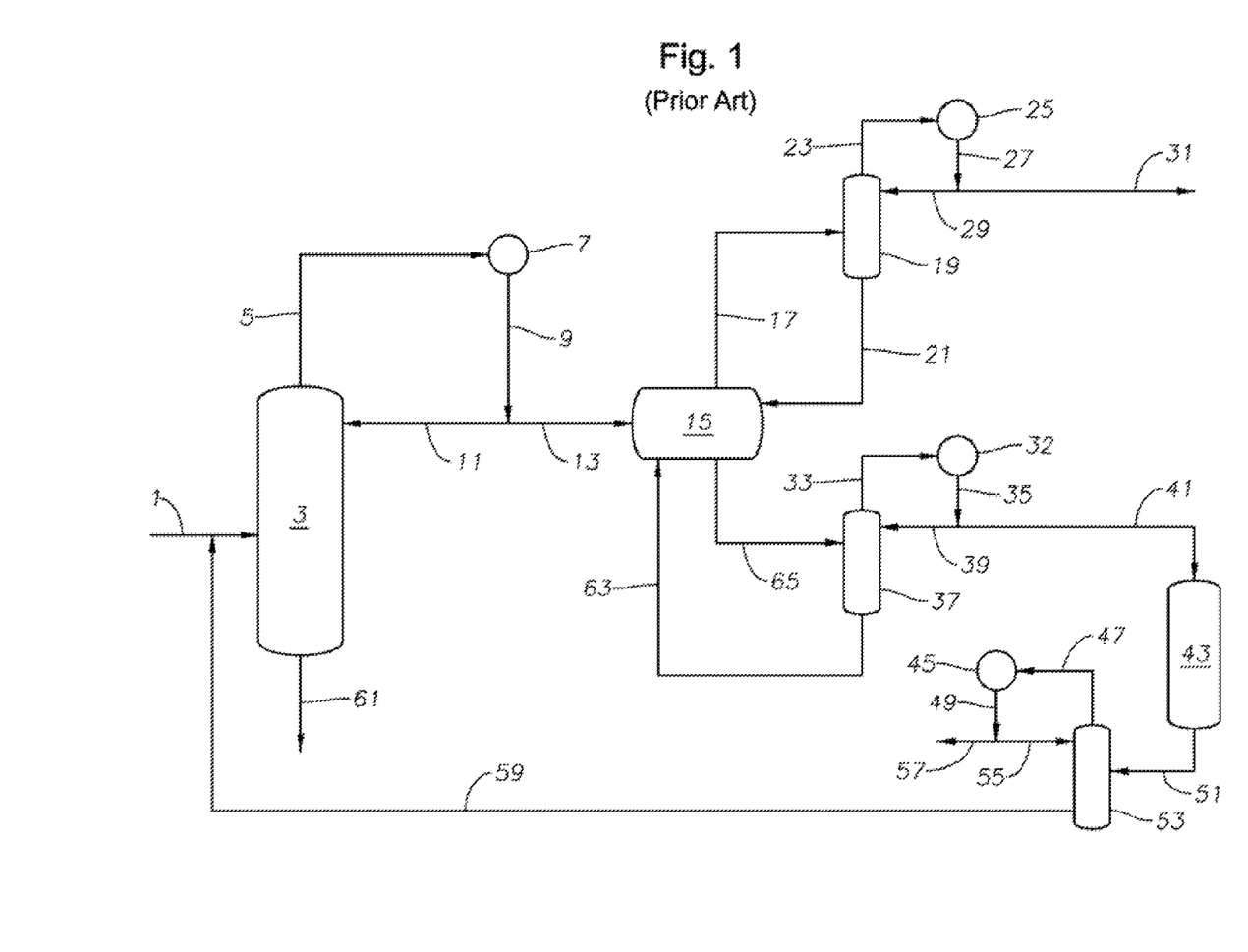
FIG. 1 is a flow diagram of a conventional para-xylene (PX) production and extraction process which employs liquid phase xylene isomerization and vapor phase xylene isomerization.

In a typical aromatics plant, liquid feed, as shown in FIG. 1, typically a $C_{8+}$ aromatic feedstream which has previously been processed by known methods to remove $C_{7-}$ species (particularly benzene and toluene), is fed by conduit 1 to a xylenes re-run column 3. The xylenes re-run column (or more simply a fractionation column) vaporizes the feed and separates the $C_8$ aromatics into an overhead mixture 5 of xylenes (OX, MX, and PX) and ethylbenzene (EB), and a bottom product 61 comprising $C_{9+}$ aromatics. The overhead mixture typically has a composition of about 40-50% metaxylene (MX), 15-25% PX, 15-25% OX, and 10-20% EB. Unless otherwise noted herein, percentages are % weight.

The overhead mixture 5 is then to the PX recovery unit 15, which may employ crystallization technology, adsorption technology, or membrane separation technology. These technologies separate PX from its isomers and are capable of producing high purity PX up to 99.9%, which is taken from unit 15 via conduit 17. In the case where unit 15 is an adsorptive separation unit, such as a Parex™ or Eluxyl™ unit, the extract 17, which comprises a desorbent, such as paradiethylbenzene (PDEB), needs to be separated, such as by distillation, from the desired extract PX in distillation column 19. This generates a high purity PX stream 27, which may contain light impurities such as toluene, non-aromatics and water that are removed in a downstream column (not shown) to further improve PX purity. The desorbent is returned to the PX recovery system 15 via conduit 21.

The raffinate 65, which comprises mainly MX, OX, EB, and desorbent is sent to fractionation column 37, generating stream 35, containing MX, OX, and EB, and bottoms 63. The desorbent in the bottoms product 63 is returned to 15. Note that as used herein the term "raffinate" is used to mean the portion recovered from the PX recovery unit 15, whether the technology used is adsorptive separation, crystallization, or membrane. The stream 35 is sent to isomerization unit 43 to isomerize the MX and OX and, optionally, EB to an equilibrium mixture of the four isomers. Isomerization unit 43 may be a vapor phase or liquid phase isomerization unit or both. The product of the isomerization unit 43 is sent via conduit 51 to the $C_{7-}$ distillation tower 53, which separates the product of isomerization into a bottom stream 59 comprising equilibrium xylenes and the overhead 47, comprising $C_{7-}$ aromatics, e.g., benzene and toluene. The bottoms product 59 of distillation tower 53 is then sent to xylenes re-run column 3, either merging with feed 1 as shown in the figure, or it may be introduced by a separate inlet (not shown).

However, the presence of EB in the $C_8$ aromatic streams may impact the efficiency of certain processes described above. In particular, when an adsorptive separation unit is used for PX recovery, while the adsorbent has a higher affinity for PX, it may also adsorb EB to a significant extent, thereby reducing the adsorbent's capacity to adsorb PX. Thus, to avoid EB competing for adsorption capacity and increase the efficiency of PX adsorption, it is desirable to reduce or minimize the amount of EB in the $C_8$ aromatic stream sent to the adsorptive separation unit. Additionally, liquid phase isomerization converts little or none of the EB in the PX-depleted stream, and as a result, the amount of EB in the xylenes loop can build up to very high levels. Thus, to maximize the use of liquid phase isomerization, it is also desirable to control the amount of EB in the PX-depleted stream subjected to liquid phase isomerization.

SUMMARY OF THE INVENTION

The present invention is an improved process for producing PX, particularly with respect to a process that involves the methylation of toluene and/or benzene to selectively produce PX, wherein streams having differing amounts of EB are separately treated in the recovery of PX. A first hydrocarbon feed comprising xylenes and EB is provided to a first PX adsorption section, where a first PX-rich stream and a first PX-depleted stream are recovered from the feed. A second hydrocarbon feed comprising xylenes and less EB than the first hydrocarbon feed is provided to a second PX adsorption section, where a second PX-rich stream and a second PX-depleted stream are recovered from the feed. Segregating the feeds with differing EB contents increases the overall efficiency of the adsorption of PX by the adsorption units. The first and second PX adsorption sections may be individual PX adsorption units or individual towers of a single PX adsorption unit. In embodiments, prior to the PX adsorption sections, the first hydrocarbon feed may be passed through a first xylenes fractionation tower to produce a first overhead stream comprising $C_8$ hydrocarbons, which is sent to the first PX adsorption section, and a first bottoms stream containing $C_{9+}$ hydrocarbons. Similarly, the second hydrocarbon feed may be passed through a second xylenes fractionation tower to produce a second overhead stream comprising $C_8$ hydrocarbons, which is sent to the second PX adsorption section, and a second bottoms stream containing $C_{9+}$ hydrocarbons.

The first and second PX-depleted streams, provided to opposite sides of the dividing wall in a divided wall raffinate column, are then separated into an EB-rich stream and an EB-depleted stream. At least part of the EB-rich stream is then fed to a xylene isomerization unit where the EB-rich stream is isomerized under at least partial vapor phase conditions to produce a first isomerized stream having a higher PX concentration than the first and second PX-depleted streams. At least part of the EB-depleted stream is then fed to a xylene isomerization unit where the EB-depleted stream is isomerized under at least partial liquid phase conditions to produce a second isomerized stream having a higher PX concentration than the first and second PX-depleted streams. Because vapor phase isomerization is more effective at converting EB than liquid phase isomerization, but liquid phase isomerization is more energy efficient, separating the PX-depleted streams based on EB content and subjecting each to the appropriate isomerization process maximizes the efficiency and effectiveness of the process. At least part of the first isomerized stream is then recycled to the first PX adsorption section or optionally the first xylenes fractionation tower, and at least part of the second isomerized stream is then recycled to the second PX adsorption section or optionally the second xylenes fractionation tower, to recover additional PX. The process is then repeated to define a so-called xylene isomerization loop.

The invention also includes an apparatus for practicing the inventive process comprising a first PX adsorption section, which produces a first PX-rich stream and a first PX-depleted stream from a first hydrocarbon feed, and a second PX adsorption section, which produces a second PX-rich stream and a second PX-depleted stream from a second hydrocarbon feed. The first and second PX adsorption sections are fluidly connected to a divided wall raffinate column in which the first and second PX-depleted streams are separated into an EB-rich stream and an EB-depleted stream. Fluidly connected to the divided wall raffinate column is a vapor phase isomerization unit that isomerizes the EB-rich stream and produces a first isomerized stream having a higher PX concentration than the first and second PX-depleted streams, and a liquid phase isomerization unit that isomerizes the EB-depleted stream and produces a second isomerized stream having a higher PX concentration than the first and second PX-depleted streams. In embodiments, a first xylenes fractionation column is fluidly connected downstream of the vapor phase isomerization unit and upstream of the first PX adsorption section, and a second xylenes fractionation column is fluidly connected downstream of the liquid phase isomerization unit and upstream of the second PX adsorption section.

DETAILED DESCRIPTION OF THE INVENTION

As used herein the term "$C_n$" hydrocarbon, wherein n is a positive integer, means a hydrocarbon having n number of carbon atom(s) per molecule. For example, a $C_8$ aromatic hydrocarbon means an aromatic hydrocarbon or mixture of aromatic hydrocarbons having 8 number of carbon atom(s) per molecule. The term "$C_n+$" hydrocarbon, wherein n is a positive integer, means a hydrocarbon having at least n number of carbon atom(s) per molecule, whereas the term "$C_-$" hydrocarbon wherein n is a positive integer, means a hydrocarbon having no more than n number of carbon atom(s) per molecule.

Figure 2:
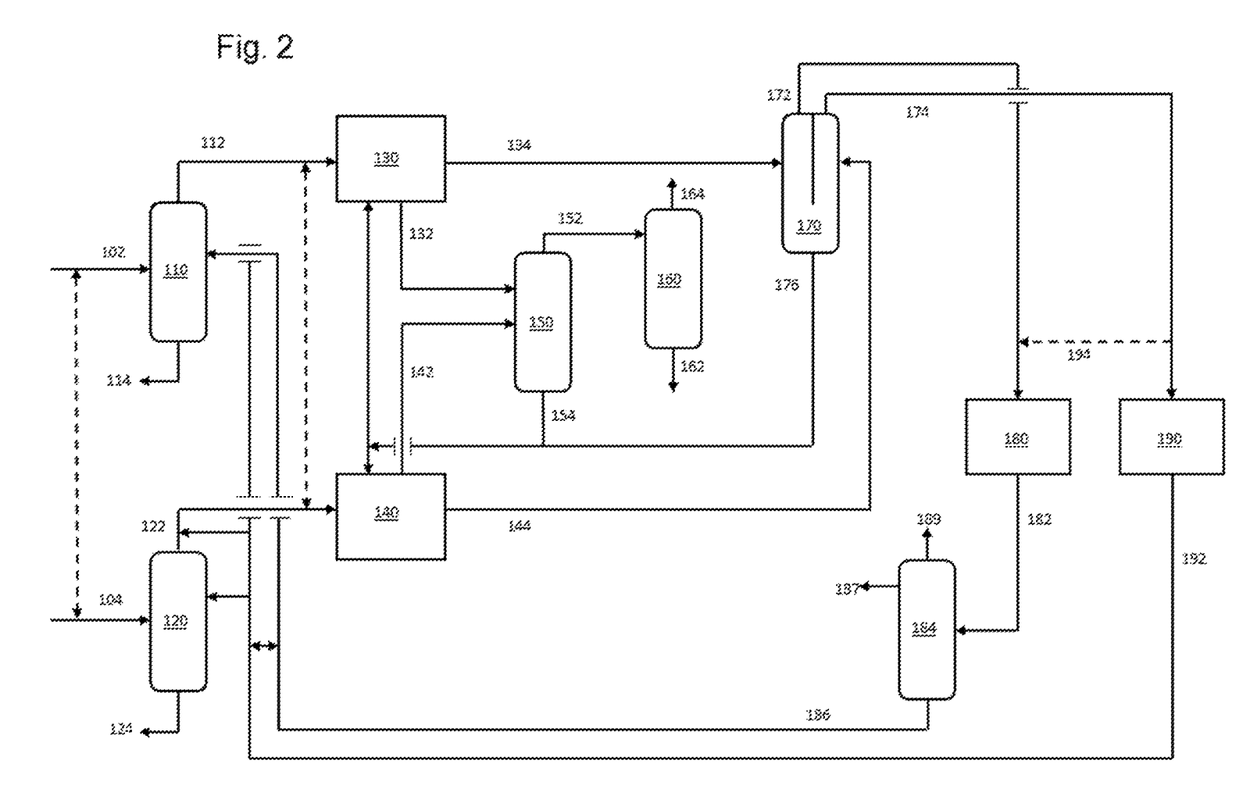
FIG. 2 is a flow diagram of one embodiment of the inventive process.

The present invention is an improved process and apparatus for producing PX, particularly with respect to a process that involves the methylation of toluene and/or benzene to selectively produce PX, wherein streams having differing amounts of ethylbenzene are separately treated to increase the efficiency of the recovery of PX. With reference to FIG. 2, a first hydrocarbon feed 102 comprising xylenes and EB is provided to a first para-xylene adsorption section 130, where a first PX-rich stream 132 and a first PX-depleted stream 134 are recovered from the feed. A second hydrocarbon feed 104 comprising xylenes and less EB than the first hydrocarbon feed 102 is provided to a second para-xylene adsorption section 140, where a second PX-rich stream 142 and a second PX-depleted stream 144 are recovered from the feed. The first and second PX-depleted streams 134, 144 are then separated into an EB-rich stream 172 and an EB-depleted stream 174 in a divided wall raffinate column 170. At least part of the EB-rich stream 172 is then fed to a xylene isomerization unit 180 where the EB-rich stream 172 is isomerized under at least partial vapor phase conditions to produce a first isomerized stream 182 having a higher PX concentration than the first and second PX-depleted streams 134, 144. At least part of the EB-depleted stream 174 is then fed to a xylene isomerization unit 190 where the EB-depleted stream 174 is isomerized under at least partial liquid phase conditions to produce a second isomerized stream 192 having a higher PX concentration than the first and second PX-depleted streams 134, 144. At least part of the first isomerized stream 182 is then recycled to the first para-xylene adsorption section 130, and at least part of the second isomerized stream 192 is then recycled to the second para-xylene adsorption section 140, to recover additional PX and the process is repeated to define a so-called xylene isomerization loop.

Hydrocarbon Feed

The first hydrocarbon feed 102 employed in the present process may be any hydrocarbon stream containing xylenes and EB, such as, but not limited to, a reformate stream (product stream of a reformate splitting tower), a hydrocracking product stream, a xylene or EB reaction product stream, an aromatic disproportionation stream, an aromatic transalkylation stream, a Cyclar™ process stream, and/or an import stream. The first feed 102 may contain at least 1.0 wt %, 2.0 wt %, 3.0 wt %, 5.0 wt %, 7.5 wt % or 10.0 wt % EB.

The second hydrocarbon feed 104 may be a hydrocarbon stream containing xylenes and less EB than the first hydrocarbon feed 102, such as, but not limited to, a PX selective aromatic alkylation product stream, a non-selective (equilibrium PX) aromatic alkylation product stream, an aromatic disproportionation stream, an aromatic transalkylation stream, a methanol/dimethyl ether to aromatic product stream, a syngas to aromatic product stream, a $C_2$-$C_4$ alkane/alkene to aromatic product stream, an import stream, and/or an off-spec PX stream from a PX recovery unit. The second feed 104 may contain less than 10.0 wt %, 7.5 wt %, 5.0 wt %, 3.0 wt %, 2.0 wt % or 1.0 wt % EB, as long as it is less than the EB content of the first feed 102.

In one embodiment, the second hydrocarbon feed 104 is the product of the selective alkylation of benzene and/or toluene with methanol and/or dimethyl ether in a methylation reactor. The reactor may be a fluidized bed, moving bed, fixed bed, cyclic, or any combination thereof. One fluidized bed methylation reactor is described in U.S. Pat. Nos. 6,423,879 and 6,504,072, the entire contents of which are incorporated herein by reference, and employs a catalyst comprising a porous crystalline material having a Diffusion Parameter for 2,2 dimethylbutane of about 0.1-15 $sec^{-1}$ when measured at a temperature of 120° C. and a 2,2 dimethylbutane pressure of 60 torr (8 kPa). The porous crystalline material may be a medium-pore zeolite, such as ZSM-5, which has been severely steamed at a temperature of at least 950° C. in the presence of at least one oxide modifier, for example, including phosphorus, to control reduction of the micropore volume of the material during the steaming step. An example of a fixed bed process and catalyst is described in U.S. Pat. Nos. 7,304,194 and 8,558, 046, which disclose a phosphorus-modified ZSM-5 catalyst steamed at a temperature of 150-350° C. to increase selectivity to para-xylene.

The feeds may further comprise recycle stream(s) from the isomerization step(s) and/or various separating steps. The hydrocarbon feed comprises PX, together with MX, OX, and EB. In addition to xylenes and EB, the hydrocarbon feedstock may also contain certain amounts of other aromatic or even non-aromatic compounds. Examples of such aromatic compounds are $C_{7-}$ hydrocarbons, such as benzene and toluene, and $C_9$+ aromatics, such as mesitylene, pseudocumene and others. These types of feedstream(s) are described in "Handbook of Petroleum Refining Processes", Eds. Robert A. Meyers, McGraw-Hill Book Company, Second Edition.

Depending on the composition of the first and second hydrocarbon feeds 102, 104, one or more initial separation steps that serve to remove $C_{7-}$ and $C_9$+ hydrocarbons from the feed may occur prior to providing the first and second hydrocarbon feeds 102, 104 to the first and second para-xylene adsorption sections 130, 140. Generally, the initial separation steps may include fractional distillation, crystallization, adsorption, a reactive separation, a membrane separation, extraction, or any combination thereof. In one embodiment, the first hydrocarbon feed 102 is passed through a first xylenes fractionation tower 110 prior to passing to the first para-xylene adsorption section 130. The first xylenes fractionation tower 110 produces a first overhead stream 112 comprising $C_8$ hydrocarbons, which is sent to the first para-xylene adsorption section 130, and a first bottoms stream 114 containing $C_{9+}$ hydrocarbons, which may be sent to a transalkylation unit (not shown).

Likewise, the second hydrocarbon feed 104 is passed through a second xylenes fractionation tower 120 prior to passing to the second para-xylene adsorption section 140. The second xylenes fractionation tower 120 produces a second overhead stream 122 comprising $C_8$ hydrocarbons, which is sent to the second para-xylene adsorption section 140, and a second bottoms stream 124 containing $C_{9+}$ hydrocarbons. The second hydrocarbon feed 104 may be subjected to phenol and styrene removal steps, such as those described in U.S. Patent Publication Nos. 2013/0324779 and 2013/0324780, the entire contents of which are incorporated herein by reference, prior or subsequent to the second xylenes fractionation tower 120. The second bottoms stream 124 may also be subjected to phenol and styrene removal steps, such as those described in U.S. Patent Publication Nos. 2013/0324779 and 2013/0324780, before passing to a transalkylation unit (not shown), optionally with first bottoms stream 114.

Depending on the material balance and equipment requirements, a portion of the first hydrocarbon feed 102 may be combined with the second hydrocarbon feed 104, or vice versa, prior to the xylenes fractionator. Likewise, a portion of the overhead stream 112 may be combined with the overhead stream 122, or vice versa, prior to the PX adsorption sections 130, 140.

Para-Xylene Recovery

The first hydrocarbon feed 102, or the first overhead stream 112 comprising $C_8$ hydrocarbons in embodiment in which first xylenes fractionator is used, is supplied to a first para-xylene adsorption section 130 to produce a first PX-rich product stream 132 and a first PX-depleted stream 134. The second hydrocarbon feed 104, or the second overhead stream 122 comprising $C_8$ hydrocarbons in embodiment in which second xylenes fractionator is used, is supplied to a second para-xylene adsorption section 140 to produce a second PX-rich product stream 142 and a second PX-depleted stream 144. In one embodiment, the first and second PX-rich product streams 132, 142 comprise at least 10 wt % PX, preferably at least 50 wt % PX, more preferably at least 70 wt % PX, even more preferably at least 80 wt % PX, most preferably at least 90 wt % PX, and ideally at least 95 wt % PX, based on the total weight of the PX rich product stream.

The first and second para-xylene adsorption sections 130, 140 are preferably simulated moving bed adsorption units, such as a PAREX™ unit or an ELUXYL™ unit. These types of separation unit(s) and their designs are described in "Perry's Chemical Engineers' Handbook", Eds. R. H. Perry, D. W. Green and J. O. Maloney, McGraw-Hill Book Company, Sixth Edition, 1984, and the previously-mentioned "Handbook of Petroleum Refining Processes." In a typical simulated moving bed adsorption unit, the adsorbent bed consisting of several sub-beds is contained within two adsorption towers connected in series. In one embodiment, the first para-xylene adsorption section 130 and second para-xylene adsorption section 140 are separate simulated moving bed adsorption units, having two adsorption towers in each section. In another embodiment, the first para-xylene adsorption section 130 and second para-xylene adsorption section 140 each comprise one tower of a single simulated moving bed adsorption unit.

Treating feeds with differing EB contents, for example, feeds with less than 1.0 wt % EB and feeds with more than 1.0 wt % EB, separately results in more efficient adsorption of PX. While the adsorbent has a higher affinity for PX, it may also adsorb EB to a significant extent, thereby reducing the adsorbent's capacity to adsorb PX. Thus, subjecting feeds with lower amounts of EB, i.e., less than 1.0 wt % EB, to a separate PX adsorption section minimizes the amount of EB competing for adsorption capacity and increases the efficiency of PX adsorption in that adsorption section, leading to more efficient adsorption of PX overall.

In FIG. 2, as in conventional simulated moving bed plant configurations, the first and second PX-rich product streams 132, 142, comprising PX and desorbent, are sent to an extract column 150 for separation, which produces a PX stream 152 and a first desorbent stream 154. The first desorbent stream 154 is recycled to the first and second para-xylene adsorption sections 130, 140, optionally through a desorbent drum. The PX stream 152 is then sent to a finishing column 160, which produces a purified PX product 162. A toluene stream 164 is recovered as an overheads product from the finishing column 160 and may be recycled back to the PX production process, preferably the selective alkylation of benzene and/or toluene with methanol and/or dimethyl ether. In a conventional simulated moving bed plant configuration, the PX-depleted streams, comprising MX, OX, EB, and desorbent, are sent to a raffinate column; however, in the present process, a divided wall raffinate column replaces the conventional raffinate tower, which will be described below.

Divided Wall Raffinate Column

With continuing reference to FIG. 2, the first and second PX-depleted streams 134, 144 pass to a divided wall raffinate column 170, replacing the conventional raffinate column (fractionator 37 in FIG. 1), which separates the first and second PX-depleted streams 134, 144 into three streams— an EB-rich stream 172, an EB-depleted stream 174, and a second desorbent stream 176. As its name implies, the term "divided wall distillation column" refers to a particular known form of distillation column which comprises a dividing wall. The dividing wall vertically bisects a portion of the interior of the distillation column but does not extend either to the top or bottom sections of the column, thus, enabling the column to be refluxed and reboiled similar to a conventional column. The dividing wall provides a fluid impermeable baffle separating the interior of the column. The divided wall column may be configured for a number of processes, with an inlet to the column located on one side of the dividing wall and one or more side draws located on the opposing side, or an inlet on both sides of the divided wall column and multiple draws from the top or bottom of the column, or any combination thereof.

In a particular embodiment, the dividing wall extends from the top of the column down to a tray on which the EB concentration is low enough to provide an optimum ratio of low EB and high EB products, which is ascertainable by one skilled in the art using simulation tools. The first PX-depleted stream 134 derived from the first hydrocarbon feed 102 having a higher EB concentration is provided to the divided wall raffinate column 170 on one side of the dividing wall, and the second PX-depleted stream 144 derived from the second hydrocarbon feed 104 having a lower EB concentration is provided to the divided wall raffinate column 170 on the opposite side of the dividing wall. The EB-rich stream 172 and the EB-depleted stream 174 are withdrawn from the top of the column or near the top of the column to remove lighter components such as water. Each overhead stream may be processed through a separate overhead product system (not shown), and a portion of the EB-rich stream 172 and EB-depleted stream 174 may be returned to the divided wall raffinate column 170 as reflux. Using a divided wall column as the raffinate column further enhances the EB separation in the PX-depleted streams, allowing for more efficient use of isomerization processes.

At least a portion of the EB-rich stream 172 is sent to isomerization unit 180, and at least a portion of the EB-depleted stream 174 is sent to isomerization unit 190. In other embodiments in which the amount of EB in the EB-rich stream is minimal, the EB-rich stream may be purged to fuel blending. The second desorbent stream 176 is recycled to the first and second para-xylene adsorption sections 130, 140, optionally through a desorbent drum.

Xylene Isomerization

Because liquid phase isomerization converts little or none of the EB in the PX-depleted stream, in a preferred embodiment, the EB-rich stream 172 is sent to isomerization unit 180, which is operated in the vapor phase, and the EB-depleted stream 174 is sent to isomerization unit 190, which is operated in the liquid phase. Minimizing the amount of PX-depleted stream subjected to vapor phase isomerization saves energy and capital, as liquid phase isomerization requires less energy and capital than the vapor phase isomerization process due to the requirement of vaporizing the PX-depleted stream and the use of hydrogen, which requires an energy- and capital-intensive hydrogen recycle loop.

Vapor Phase Isomerization

The EB-rich stream 172 is fed to a xylene isomerization unit 180 where the EB-rich stream 172 is contacted with a xylene isomerization catalyst under at least partially vapor phase conditions effective to isomerize the PX-depleted, EB-rich stream 172 back towards an equilibrium concentration of the xylene isomers. There are generally two types of vapor phase isomerization catalysts—one that dealkylates EB to produce benzene and ethylene and isomerizes the xylene isomers, and one that isomerizes the four different C8 aromatic compounds, including EB, to their equilibrium concentrations. Either catalyst may be used for the vapor phase isomerization unit 180.

EB Dealkylation

In one embodiment, the EB-rich stream 172 is subjected to xylenes isomerization in which the EB in the stream can be dealkylated to produce benzene. In this embodiment, where the ethylbenzene is removed by cracking/disproportionation, the para-xylene-depleted $C_8$ stream is conveniently fed to a multi-bed reactor comprising at least a first bed containing an ethylbenzene conversion catalyst and a second bed downstream of the first bed and containing a xylene isomerization catalyst. The beds can be in the same or different reactors. Alternatively, the ethylbenzene conversion catalyst and xylene isomerization catalyst may be contained in a single bed reactor.

The ethylbenzene conversion catalyst typically comprises an intermediate pore size zeolite having a Constraint Index ranging from 1 to 12, a silica to alumina molar ratio of at least about 5, such as at least about 12, for example at least 20, and an alpha value of at least 5, such as 75 to 5000. Constraint Index and its method of determination are disclosed in U.S. Pat. No. 4,016,218, which is herein incorporated by reference, whereas the alpha test is described in U.S. Pat. No. 3,354,078 and in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, p. 395. Higher alpha values correspond with a more active cracking catalyst.

Examples of suitable intermediate pore size zeolites include ZSM-5 (U.S. Pat. Nos. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); ZSM-58 (U.S. Pat. No. 4,417,780); EU-1; and mordenite. The entire contents of the above references are incorporated by reference herein. Preferred zeolites are ZSM-5, ZSM-12 or EU-1.

The zeolite employed in ethylbenzene conversion catalyst typically has a crystal size of at least 0.2 microns and exhibits an equilibrium sorption capacity for xylene, which can be either para, meta, ortho, or a mixture thereof, of at least 1 gram per 100 grams of zeolite measured at 120° C. and a xylene pressure of 4.5±0.8 mm of mercury and an ortho-xylene sorption time for 30 percent of its equilibrium ortho-xylene sorption capacity of greater than 1200 minutes (at the same conditions of temperature and pressure). The sorption measurements may be carried out gravimetrically in a thermal balance. The sorption test is described in U.S. Pat. Nos. 4,117,026; 4,159,282; 5,173,461; and Re. 31,782, each of which is incorporated by reference herein.

The zeolite used in the ethylbenzene conversion catalyst may be self-bound (no binder) or may be composited with an inorganic oxide binder, with the zeolite content ranging from between about 1 to about 99 percent by weight and more usually in the range of about 10 to about 80 percent by weight of the dry composite, e.g., about 65% zeolite with about 35% binder. Where a binder is used, it is preferably non-acidic, such as silica. Procedures for preparing silica bound ZSM-5 are described in U.S. Pat. Nos. 4,582,815; 5,053,374; and 5,182,242, incorporated by reference herein.

In addition, the ethylbenzene conversion catalyst typically comprises from about 0.001 to about 10 percent by weight, e.g., from about 0.05 to about 5 percent by weight, e.g., from about 0.1 to about 2 percent by weight of a hydrogenation/dehydrogenation component. Examples of such components include the oxide, hydroxide, sulfide, or free metal (i.e., zero valent) forms of Group VIIIA metals (i.e., Pt, Pd, Ir, Rh, Os, Ru, Ni, Co, and Fe), Group VIIA metals (i.e., Mn, Tc, and Re), Group VIA metals (i.e., Cr, Mo, and W), Group VB metals (i.e., Sb and Bi), Group IVB metals (i.e., Sn and Pb), Group IIIB metals (i.e., Ga and In), and Group IB metals (i.e., Cu, Ag and Au). Noble metals (i.e., Pt, Pd, Ir, Rh, Os and Ru) are preferred hydrogenation/dehydrogenation components. Combinations of catalytic forms of such noble or non-noble metal, such as combinations of Pt with Sn, may be used. The metal may be in a reduced valence state, e.g., when this component is in the form of an oxide or hydroxide. The reduced valence state of this metal may be attained, in situ, during the course of a reaction, when a reducing agent, such as hydrogen, is included in the feed to the reaction.

The xylene isomerization catalyst employed in this embodiment typically comprises an intermediate pore size zeolite, e.g., one having a Constraint Index between 1 and 12, specifically ZSM-5. The acidity of the ZSM-5 of this catalyst, expressed as the alpha value, is generally less than about 150, such as less than about 100, for example from about 5 to about 25. Such reduced alpha values can be obtained by steaming. The zeolite typically has a crystal size less than 0.2 micron and an ortho-xylene sorption time such that it requires less than 50 minutes to sorb ortho-xylene in an amount equal to 30% of its equilibrium sorption capacity for ortho-xylene at 120° C. and a xylene pressure of 4.5+0.8 mm of mercury. The xylene isomerization catalyst may be self-bound form (no binder) or may be composited with an inorganic oxide binder, such as alumina. In addition, the xylene isomerization catalyst may contain the same hydrogenation/dehydrogenation component as the ethylbenzene conversion catalyst.

Using the catalyst system described above, ethylbenzene cracking/disproportionation and xylene isomerization are typically effected at conditions including a temperature of from about 400° F. to about 1,000° F. (204 to 538° C.), a pressure of from about 0 to about 1,000 psig (100 to 7,000 kPa), a weight hourly space velocity (WHSV) of between about 0.1 and about 200 hr−1, and a hydrogen, $H_2$ to hydrocarbon, HC, molar ratio of between about 0.1 and about 10. Alternatively, the conversion conditions may include a temperature of from about 650° F. and about 900° F. (343 to 482° C.), a pressure from about 50 and about 400 psig (446 to 2,859 kPa), a WHSV of between about 3 and about 50 hr−1 and a $H_2$ to HC molar ratio of between about 0.5 and about 5. The WHSV is based on the weight of catalyst composition, i.e., the total weight of active catalyst plus, if used, binder therefor.

EB Isomerization

In another embodiment, the EB-rich stream 172 is subjected to EB isomerization to produce a stream containing the $C_8$ aromatic compounds in equilibrium concentrations.

Typically, the EB isomerization catalyst comprises an intermediate pore size molecular sieve having a Constraint Index within the approximate range of 1 to 12, such as ZSM-5 (U.S. Pat. No. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780). Alternatively, the xylene isomerization catalyst may comprise a molecular sieve selected from MCM-22 (described in U.S. Pat. No. 4,954,325); PSH-3 (described in U.S. Pat. No. 4,439,409); SSZ-25 (described in U.S. Pat. No. 4,826,667); MCM-36 (described in U.S. Pat. No. 5,250,277); MCM-49 (described in U.S. Pat. No. 5,236,575); and MCM-56 (described in U.S. Pat. No. 5,362,697). The molecular sieve may also comprise a EUO structural type molecular sieve, with EU-1 being preferred, or mordenite. A preferred molecular sieve is one of the EUO structural type having a Si/Al ratio of about 10-25, as disclosed in U.S. Pat. No. 7,893,309. The entire contents of the above references are incorporated by reference herein.

It may be desirable to combine the molecular sieve of the xylene isomerization catalyst with another material resistant to the temperature and other conditions of the process. Such matrix materials include synthetic or naturally occurring substances as well as inorganic materials such as clay, silica, and/or metal oxides (such as titanium oxide or boron oxide). The metal oxides may be naturally occurring or in the form of gelatinous precipitates or gels including mixtures of silica and metal oxides. Naturally occurring clays, which can be composited with the molecular sieve, include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification.

In addition to the foregoing materials, the molecular sieve may be composited with a porous matrix material, such as alumina, zirconia, silica-alumina, silica-magnesia, silica-zirconia, silica-thoria, silica-berylia, silica-titanic, aluminum phosphates, titanium phosphates, zirconia phosphates, as well as ternary compounds such as silica-alumina-thoria, silica-alumina-zirconia, silica-alumina-magnesia, and silica-magnesia-zirconia. A mixture of these components could also be used. The matrix may be in the form of a cogel. The relative proportions of molecular sieve component and inorganic oxide gel matrix on an anhydrous basis may vary widely with the molecular sieve content ranging from between about 1 to about 99 percent by weight and more usually in the range of about 10 to about 80 percent by weight of the dry composite.

The EB isomerization catalyst also comprises at least one metal from Group VIII of the periodic table of the elements and optionally at least one metal selected from metals from Groups IIIA, IVA, and VIIB. The Group VIII metal present in the catalyst used in the isomerization process of the invention is selected from iron, cobalt, nickel, ruthenium, rhodium, palladium, osmium, iridium, and platinum, preferably from the noble metals and highly preferably from palladium and platinum. More preferably, the Group VIII metal is platinum. The metal selected from groups IIIA, IVA, and VIIB which are optionally present is selected from gallium, indium, tin, and rhenium, preferably from indium, tin, and rhenium.

The conditions employed in the EB isomerization process generally include a temperature of from 300 to about 500° C., preferably from about 320 to about 450° C. and more preferably from about 340 to about 430° C.; a partial pressure of hydrogen from about 0.3 to about 1.5 MPa, preferably from about 0.4 to about 1.2 MPa, and more preferably from about 0.7 to about 1.2 Mpa; a total pressure of from about 0.45 to about 1.9 MPa, preferably from about 0.6 to about 1.5 MPa; and a weight hourly space velocity (WHSV) of between about 0.25 and about 30 $hr^{-1}$, preferably between about 1 and about 10 $hr^{-1}$ and more preferably between about 2 and about 6 $hr^{-1}$.

The product of the vapor phase xylene isomerization process 180 is a first isomerized stream 182 having a higher PX concentration than the first and second PX-depleted streams 134, 144. The first isomerized stream 182 is then recycled to the first para-xylene adsorption section 130 to recover additional PX and the process is repeated to generate a so-called xylene isomerization loop. In embodiments, the first isomerized stream 182 is passed through a detoluenizing fractionation column 184 to produce at least one $C_{7-}$ isomerized stream and a $C_{8+}$ isomerized stream 186, which is passed through the first xylenes fractionation column 110, before being recycled to the first para-xylene adsorption section 130 to recover additional PX. Preferably, the detoluenizing fractionation column 184 produces two $C_{7-}$ isomerized streams—a benzene and/or toluene stream 187 that may be sent to extraction and a light ends/hydrogen stream 189 that may be sent to fuel.

Liquid Phase Isomerization

The EB-depleted stream 174 is fed to a xylene isomerization unit 190 where the EB-depleted stream 174 is contacted with a xylene isomerization catalyst under at least partially liquid phase conditions effective to isomerize the PX-depleted, EB-depleted stream 174 back towards an equilibrium concentration of the xylene isomers. Suitable conditions for the liquid phase isomerization include a temperature of from about 200° C. to about 540° C., preferably from about 230° C. to about 310° C., and more preferably from about 270° C. to about 300° C., a pressure of from about 0 to 6,895 kPa(g), preferably from about 1,300 kPa(g) to about 3,500 kPa(g), a weight hourly space velocity (WHSV) of from 0.5 to 100 $hr^{-1}$, preferably from 1 to 20 $hr^{-1}$, and more preferably from 1 to 10 $hr^{-1}$. Generally, the conditions are selected so that a portion, preferably at least 25 wt %, and more preferably at least 50 wt %, and ideally 100 wt % of the $C_8$ aromatics would be expected to be in the liquid phase. Low levels of hydrogen, below the solubility limit, may be added to the liquid phase isomerization process.

Any catalyst capable of isomerizing xylenes in the liquid phase can be used in the xylene isomerization unit, but in one embodiment the catalyst comprises an intermediate pore size zeolite having a Constraint Index between 1 and 12. Constraint Index and its method of determination are described in U.S. Pat. No. 4,016,218, which is incorporated herein by reference. Particular examples of suitable intermediate pore size zeolites include ZSM-5, ZSM-11, ZSM-12, ZSM-22, ZSM-23, ZSM-35, ZSM-48, and MCM-22, with ZSM-5 and ZSM-11 being particularly preferred, specifically ZSM-5. It is preferred that the acidity of the zeolite, expressed as its alpha value, be greater than 300, such as greater than 500, or greater than 1,000. The alpha test is described in U.S. Pat. No. 3,354,078; in the Journal of Catalysis, Vol. 4, p. 527 (1965); Vol. 6, p. 278 (1966); and Vol. 61, p. 395 (1980), each incorporated herein by reference as to that description. The experimental conditions of the test used to determine the alpha values cited herein include a constant temperature of 538° C. and a variable flow rate as described in detail in the Journal of Catalysis, Vol. 61, p. 395. A preferred catalyst is described in U.S. Pat. No. 8,569,559, which is incorporated herein by reference.

The product of the liquid phase xylene isomerization unit 190 is a second isomerized stream 192 having a higher PX concentration than the first and second PX-depleted streams 134, 144. The second isomerized stream 192 is then recycled to first para-xylene adsorption section 130 or second para-xylene adsorption section 140 to recover additional PX and the process is repeated to generate a so-called xylene isomerization loop. To manage the level of EB in the liquid phase isomerization loop and prevent a buildup of EB, a purge stream 194 may be removed from upstream or downstream of the liquid phase xylene isomerization unit 190 at regular intervals (which may be determined by one skilled in the art) and passed to the xylene isomerization unit 180 where the EB may be converted.

Conducting xylenes isomerization under liquid phase conditions produces less $C_{9+}$ aromatics than xylenes isomerization under vapor phase conditions. Therefore, the second isomerized stream 192 may be provided to the second xylenes fractionation tower 120 at a higher tray location than the second hydrocarbon feed 104, yielding greater energy savings. Furthermore, a significant portion of the second isomerized stream 192 may bypass the second xylenes fractionation tower 120 and directly enter the second para-xylene adsorption section 140, thereby saving energy by avoiding the re-fractionation altogether.

In situations where only a single simulated moving bed unit is used conventionally, or where it is not feasible to segregate feeds with differing levels of EB, it is advantageous to segregate high PX feeds and low PX feeds as taught in U.S. Pat. Nos. 5,750,820 and 8,529,757, the entire contents of the above references are incorporated by reference herein. In order to provide high PX feeds separately from low PX feeds to the PX recovery unit and avoid the use of separate xylenes fractionation columns, a divided wall column may be used.

Figure 3:
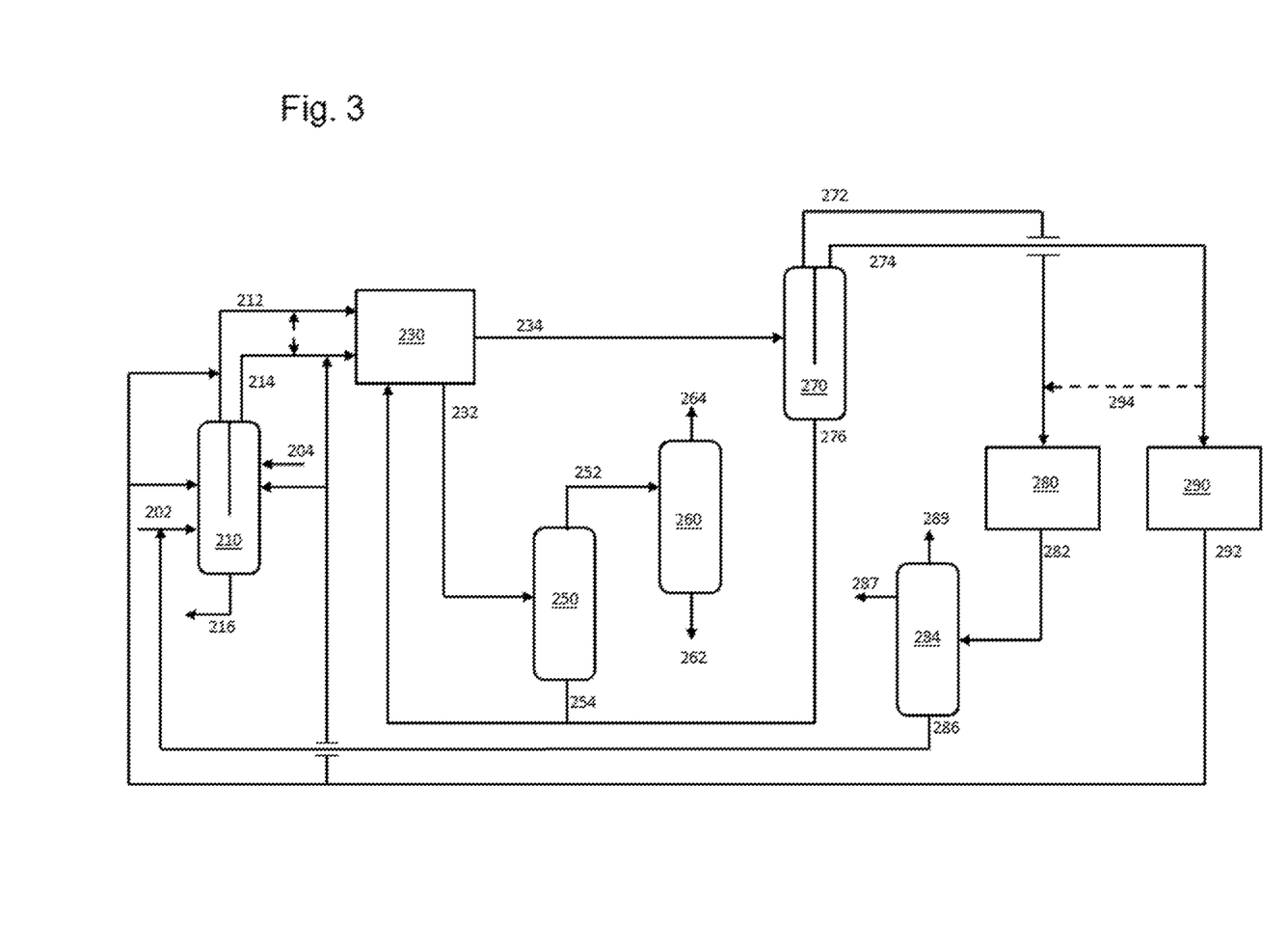
FIG. 3 is a flow diagram of a second embodiment of the inventive process.

In the embodiment shown in FIG. 3, a hydrocarbon feed 202 containing equilibrium xylenes is provided to a divided wall xylenes fractionation column 210 and a hydrocarbon feed 204 containing PX in an amount higher than its equilibrium concentration is provided to the column 210 on other side of the dividing wall. The feed 204 may be supplied at a higher tray position due to its higher concentration of PX or to its lower concentration of $C_{9+}$ aromatics, typically found in toluene methylation or toluene disproportionation product streams, which may be determined by one skilled in the art. The feed 202 may be any hydrocarbon stream containing xylenes in their equilibrium concentrations, i.e., about 22-24 wt % PX, such as a reformate stream (product stream of a reformate splitting tower), a hydrocracking product stream, a xylene or EB reaction product stream, an aromatic disproportionation stream, an aromatic transalkylation stream, a non-selective aromatic alkylation product stream, a methanol to aromatic product stream, a Cyclar™ process stream, and/or an import stream. The feed 204 may be a hydrocarbon stream containing more than about 22-24 wt % PX, such as a PX selective aromatic alkylation product stream, an aromatic disproportionation stream, an aromatic transalkylation stream, an off-spec PX stream from a PX recovery unit, an intermediate stream from a crystallizer unit, and/or an import stream.

The divided wall xylenes fractionation column 210 separates the feeds 202, 204 into three streams—an equilibrium PX stream 212, an enhanced PX stream 214, and a bottoms stream 216 containing $C_{9+}$ hydrocarbons. The bottoms stream 216 containing $C_{9+}$ hydrocarbons may be sent to a transalkylation unit to produce additional benzene, toluene and/or xylenes. The equilibrium PX stream 212 and enhanced PX stream 214 are provided to a PX recovery unit 230, preferably a simulated moving bed adsorption unit, which produces a PX-rich product stream 232 and a PX-depleted stream 234. The PX-rich product stream 232, comprising PX and desorbent, is sent to an extract column 250 for separation, which produces a PX stream 252 and a desorbent stream 254. The desorbent stream 254 is recycled to the PX recovery unit 230, optionally through a desorbent drum. The PX stream 252 is then sent to a finishing column 260, which produces a purified PX product 262. A toluene stream 264 is recovered as an overheads product from the finishing column 260 and may be recycled back to the PX production process, preferably the selective alkylation of benzene and/or toluene with methanol and/or dimethyl ether. In a conventional simulated moving bed plant configuration, the PX-depleted streams, comprising MX, OX, EB, and desorbent, are sent to a raffinate column; however, in the present process, a divided wall raffinate column replaces the conventional raffinate tower.

The PX-depleted stream 234 passes to a divided wall raffinate column 270, replacing the conventional raffinate column (fractionator 37 in FIG. 1), which separates the PX-depleted stream 234 into three streams—an EB-rich stream 272, an EB-depleted stream 274, and a desorbent stream 276. At least a portion of the EB-rich stream 272 is sent to isomerization unit 280, which is operated in the vapor phase, and at least a portion of the EB-depleted stream 274 is sent to isomerization unit 290, which is operated in the liquid phase. The desorbent stream 276 is recycled to the PX recovery unit 230, optionally through a desorbent drum.

The product of the vapor phase xylene isomerization unit 280 is a vapor-phase isomerized stream 282 having a higher PX concentration than the PX-depleted stream 234. The vapor-phase isomerized stream 282 is then recycled to the PX recovery unit 230 to recover additional PX and the process is repeated to generate a so-called xylene isomerization loop. In embodiments, the vapor-phase isomerized stream 282 is passed through a detoluenizing fractionation column 284 to produce at least one $C_{7-}$ isomerized stream and a $C_{8+}$ isomerized stream 286, which is passed through the divided wall xylenes fractionation column 210, before being recycled to the PX recovery unit 230 to recover additional PX. Preferably, the detoluenizing fractionation column 284 produces two $C_{7-}$ isomerized streams—a benzene and/or toluene stream 287 that may be sent to extraction and a light ends/hydrogen stream 289 that may be sent to fuel.

The product of the liquid phase xylene isomerization unit 290 is a liquid-phase isomerized stream 292 having a higher PX concentration than the PX-depleted stream 234. The liquid-phase isomerized stream 292 is then recycled to the PX recovery unit 230 to recover additional PX and the process is repeated to generate a so-called xylene isomerization loop. To manage the level of EB in the liquid phase isomerization loop and prevent a buildup of EB, a purge stream 294 may be removed from upstream or downstream of the liquid phase xylene isomerization unit 290 at regular intervals (which may be determined by one skilled in the art) and passed to the xylene isomerization unit 280 where the EB may be converted. The liquid-phase isomerized stream 292 may first pass through the divided wall xylenes fractionation column 210, on either side of the dividing wall, or be provided to the PX recovery unit 230 with either the equilibrium PX stream 212 or enhanced PX stream 214.

Figure 4:
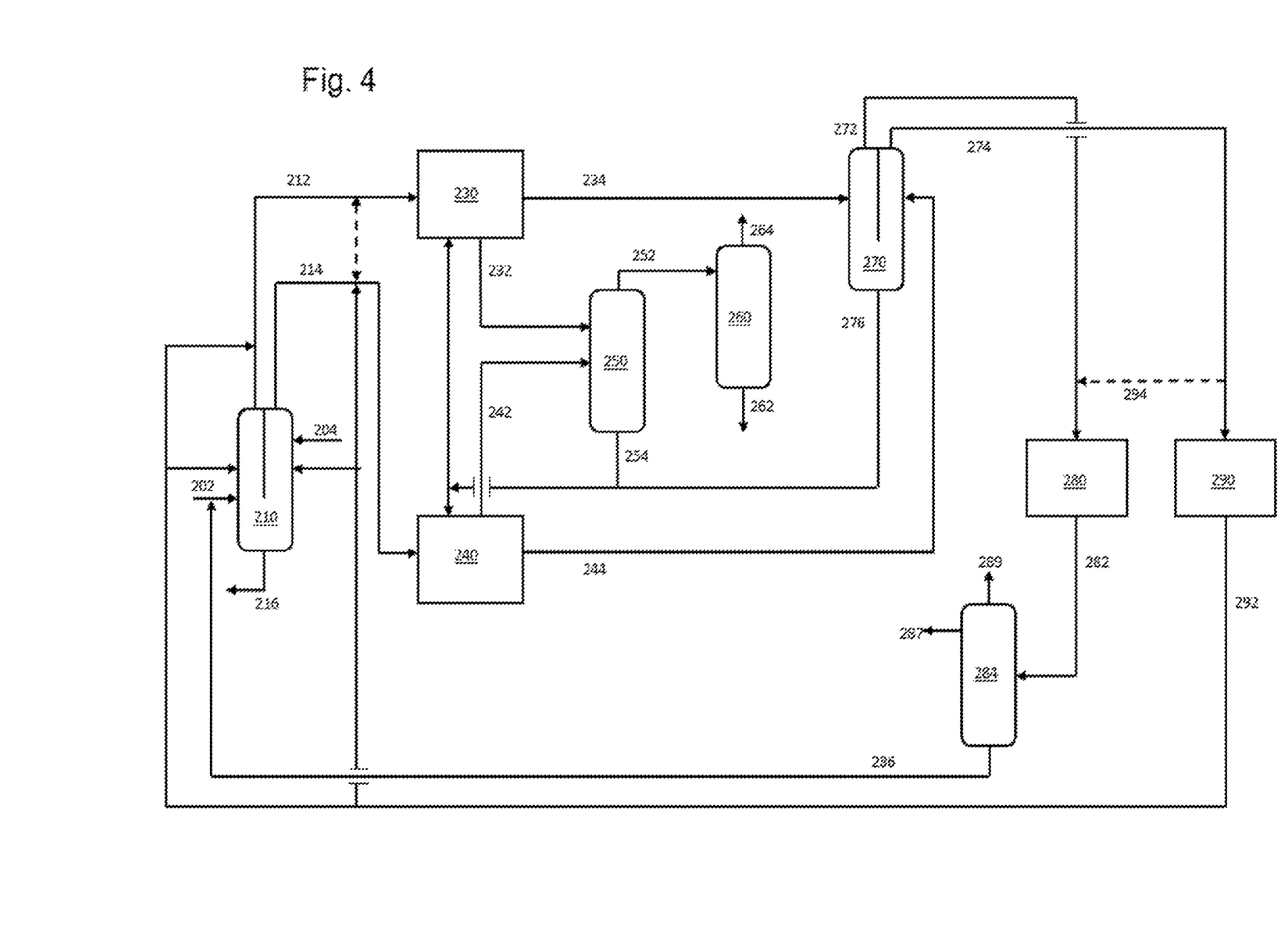
FIG. 4 is a flow diagram of a third embodiment of the inventive process.

FIG. 4 depicts an embodiment in which a divided wall xylenes fractionation column is used in conjunction with two PX adsorption sections. Corresponding elements from FIG. 3 use the same reference numerals in FIG. 4. A hydrocarbon feed 202 containing equilibrium xylenes is provided to a divided wall xylenes fractionation column 210 and a hydrocarbon feed 204 containing PX in an amount higher than its equilibrium concentration is provided to the column 210 on other side of the dividing wall. The divided wall xylenes fractionation column 210 separates the feeds 202, 204 into three streams—an equilibrium PX stream 212, an enhanced PX stream 214, and a bottoms stream 216 containing $C_{9+}$ hydrocarbons.

The equilibrium PX stream 212 is provided to a first PX recovery unit 230, preferably a simulated moving bed adsorption unit, which produces a PX-rich product stream 232 and a PX-depleted stream 234. The enhanced PX stream 214 is provided to a first PX recovery unit 240, preferably a simulated moving bed adsorption unit, which produces a PX-rich product stream 242 and a PX-depleted stream 244. The PX-rich product streams 232, 242, comprising PX and desorbent, are sent to an extract column 250 for separation, and the PX-depleted streams 234, 244 pass to a divided wall raffinate column 270. The remainder of the steps are similar to those described above with FIG. 3.

Figure 5:
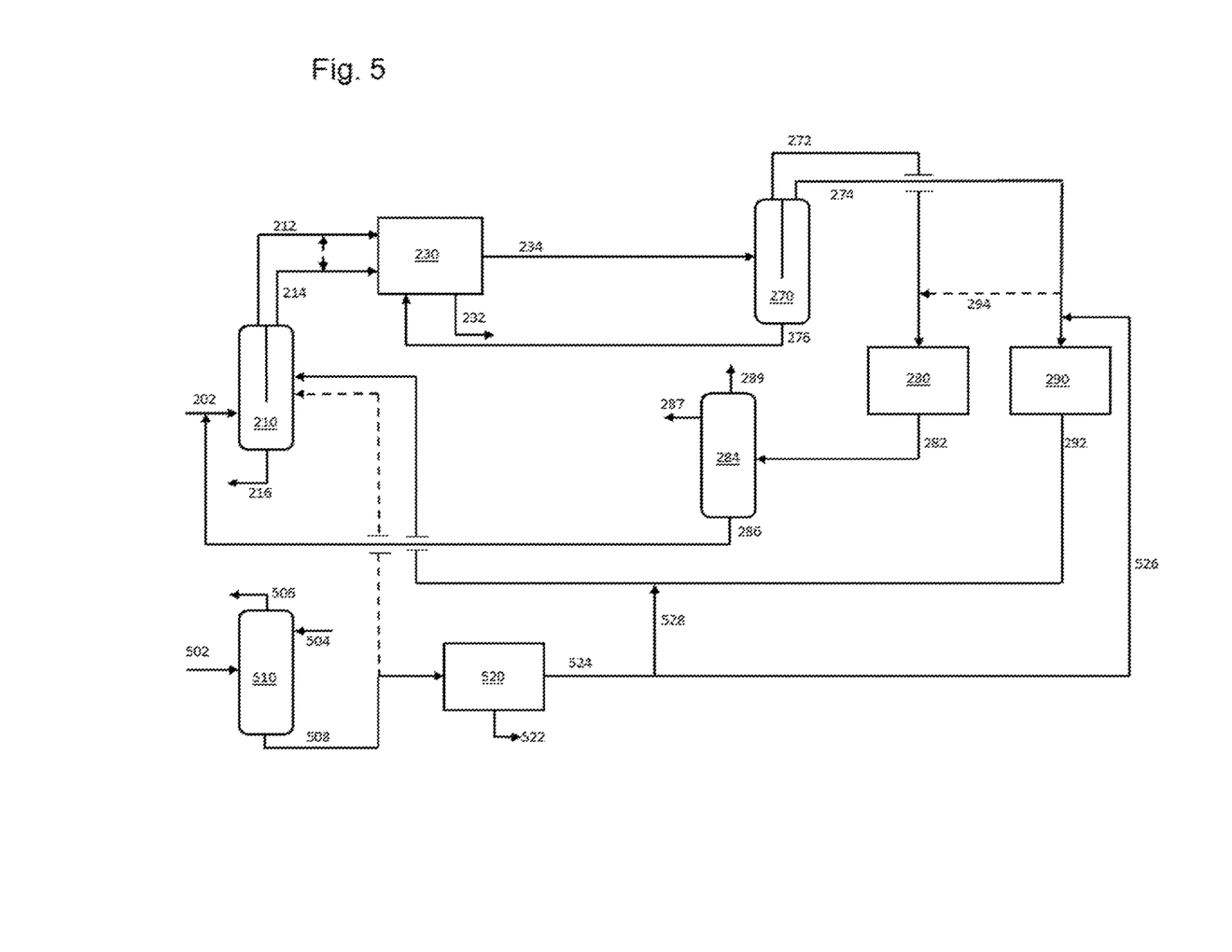
FIG. 5 is a flow diagram of a fourth embodiment of the inventive process.

FIG. 5 depicts an embodiment in which a crystallizer is used to recover PX from the product of the selective alkylation of benzene and/or toluene with methanol and/or dimethyl ether. Corresponding elements from FIGS. 3 and 4 use the same reference numerals in FIG. 5. A product stream 502 from the selective alkylation of benzene and/or toluene with methanol and/or dimethyl ether in a methylation reactor is provided to a toluene fractionation tower 510, to which a fresh toluene 504 may also be provided. The toluene fractionation tower produces an overhead toluene stream 506 that is recycled back to the methylation reactor (not shown) and a $C_{8+}$ bottoms stream 508 that is provided to a crystallizer 520. The $C_{8+}$ bottoms stream 508 may contain $C_{9+}$ aromatics, such as trimethylbenzene, methylethylbenzene, tetramethylbenzene, naphthalene, and heavy oxygenates, but as taught by U.S. Pat. No. 8,907,152, the $C_{8+}$ bottoms stream 508 may contain up to 10 wt % $C_{9+}$ aromatics before necessitating fractionation upstream of the crystallizer 520. Optionally, $C_{8+}$ bottoms stream 508 may be provided to the divided wall xylenes fractionation column 210.

The crystallizer 520 may be operated at about −20° F. with propylene refrigeration or about −80° F. with ethylene refrigeration, as may be determined by one skilled in the art. Operating the crystallizer 520 at about −20° F. with propylene refrigeration produces a filtrate 524 with about 30 wt % PX and about 3-4 wt % of EB, while operating the crystallizer 520 at about −80° F. with ethylene refrigeration produces a filtrate 524 with about 10 wt % PX and about 4-5 wt % of EB.

If the filtrate 524 contains less than about 22-24 wt % PX, such as when ethylene refrigeration is used, then the filtrate 524 is sent to the liquid phase isomerization unit 290 to isomerize the xylenes. If the filtrate 524 contains more than about 22-24 wt % PX, such as when propylene refrigeration is used, then the filtrate 524 is sent to the divided wall xylenes fractionation column 210. The remaining steps follow the embodiments shown in FIGS. 3 and 5. The PX recovery section of FIG. 5, depicted as PX recovery unit 230, may follow the single PX recovery unit embodiment as shown in FIG. 3 or the two section PX recovery unit embodiment as shown in FIG. 4.

While the present invention has been described and illustrated by reference to particular embodiments, those of ordinary skill in the art will appreciate that the invention lends itself to variations and modification is not necessarily illustrated herein without departing from the spirit and scope of the invention.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

The invention claimed is:

1. A process for producing para-xylene, the process comprising:
    (a) providing a first hydrocarbon feed comprising para-xylene, meta-xylene, ortho-xylene, and ethylbenzene to a first para-xylene adsorption section;
    (b) providing a second hydrocarbon feed comprising para-xylene, meta-xylene, ortho-xylene, and less ethylbenzene than the first hydrocarbon feed to a second para-xylene adsorption section;
    (c) recovering a first para-xylene-rich stream and a first para-xylene-depleted stream from the first hydrocarbon feed from the first para-xylene adsorption section;
    (d) recovering a second para-xylene-rich stream and a second para-xylene-depleted stream from the second hydrocarbon feed from the second para-xylene adsorption section;
    (e) separating the first and second para-xylene-depleted streams into an ethylbenzene-rich stream, which contains a majority portion of the ethylbenzene from the first and second para-xylene-depleted streams, and an ethylbenzene-depleted stream, which contains a minor portion of the ethylbenzene from the first and second para-xylene-depleted streams, in a divided wall raffinate column, wherein the first and second para-xylene-depleted streams are provided to the divided wall raffinate column on opposite sides of the dividing wall;
    (f) isomerizing meta-xylene, ortho-xylene, and ethylbenzene in at least a portion of the ethylbenzene-rich stream at least partially in the vapor phase back towards to an equilibrium concentration of xylene isomers to produce a second isomerized stream having a higher para-xylene concentration than the para-xylene-depleted stream;
    (g) isomerizing at least a portion of the ethylbenzene-depleted stream at least partially in the liquid phase back towards an equilibrium concentration of the xylenes isomers to produce a first isomerized stream having a higher para-xylene concentration than the para-xylene-depleted stream;
    (h) recycling at least a portion of the first isomerized stream to the first para-xylene adsorption section; and
    (i) recycling at least a portion of the second isomerized stream to the second para-xylene adsorption section.

2. The process of claim 1, wherein the first and second para-xylene adsorption sections each comprise two simulated moving bed adsorption towers.

3. The process of claim 1, wherein the first and second para-xylene adsorption sections each comprise one simulated moving bed adsorption tower.

4. The process of claim 1, wherein the first hydrocarbon feed comprises at least about 10.0 wt % of ethylbenzene and the second hydrocarbon feed comprises less than about 10.0 wt % ethylbenzene.

5. The process of claim 1, wherein step (f) is conducted under ethylbenzene dealkylation conditions.

6. The process of claim 1, wherein step (f) is conducted under ethylbenzene isomerization conditions.

7. The process of claim 1, wherein the first hydrocarbon feed is selected from the group consisting of a reformate stream, a hydrocracking product stream, a xylene or EB reaction product stream, an aromatic disproportionation stream, an aromatic transalkylation stream, and mixture thereof.

8. The process of claim 1, wherein the second hydrocarbon feed is selected from the group consisting of a para-selective aromatic alkylation product stream, a non-selective aromatic alkylation product stream, an aromatic disproportionation stream, an aromatic transalkylation stream, a methanol/dimethyl ether to aromatic product stream, a syngas to aromatic product stream, a $C_2$-$C_4$ alkane/alkene to aromatic product stream, an import stream, and/or an off-spec PX stream from a PX recovery unit.

9. The process of claim 1, wherein the second hydrocarbon feed comprises a selective benzene and/or toluene methylation product stream.

10. The process of claim 9, wherein the selective benzene and/or toluene methylation product stream is produced in a fluid bed, fixed bed, moving bed, or cyclic bed reactor.

11. The process of claim 1, further comprising separating at least one $C_{7-}$ isomerized stream from the first isomerized stream in a detoluenizing fractionation column prior to step (h).

12. The process of claim 1, wherein step (a) further comprises separating a $C_{9+}$ stream from the first hydrocarbon feed in a first xylenes fractionation column prior to providing the first hydrocarbon feed to the first para-xylene adsorption section, and wherein step (b) further comprises separating a $C_{9+}$ stream from the second hydrocarbon feed in a second xylenes fractionation column prior to providing second hydrocarbon feed to the second para-xylene adsorption section.

13. The process of claim 12, further comprising providing the first isomerized stream to the first xylenes fractionation column prior to step (h).

14. The process of claim 12, further comprising providing the second isomerized stream to the second xylenes fractionation column prior to step (i).

15. The process of claim 14, wherein the second isomerized stream is provided to the second xylenes fractionation column at a higher location than the second hydrocarbon feed.

* * * * *